United States Patent [19]

Aberson et al.

[11] Patent Number: 4,548,847
[45] Date of Patent: Oct. 22, 1985

[54] DELAYED-SWELLING ABSORBENT SYSTEMS

[75] Inventors: Gerard M. Aberson, Cobb County; Gerard J. F. Ring, Cherokee County, both of Ga.

[73] Assignee: Kimberly-Clark Corporation, Neenah, Wis.

[21] Appl. No.: 569,417

[22] Filed: Jan. 9, 1984

[51] Int. Cl.⁴ .................. A61F 13/20; B32B 5/26; C09K 3/00; C09K 3/32; F26B 5/16

[52] U.S. Cl. ............................... 428/74; 34/9; 34/42; 34/DIG. 1; 128/132 D; 128/156; 252/194; 428/201; 428/247; 428/286; 428/290; 428/311.9; 428/913; 524/186; 524/236; 524/417; 524/916; 525/329.8; 525/329.9; 525/367; 525/371; 525/374; 525/383; 536/76; 536/101; 536/102; 536/124; 604/364; 604/368

[58] Field of Search ............ 604/368, 364; 34/9; 34/42, DIG. 1; 128/132 D, 156; 252/194; 428/74, 201, 247, 286, 290, 311.9, 913; 524/186, 236, 417, 916; 525/329.8, 329.9, 363, 366, 367, 370, 371, 374, 383; 536/76, 101, 102, 124

[56] References Cited

U.S. PATENT DOCUMENTS

| | | |
|---|---|---|
| 2,810,716 | 10/1957 | Markus . |
| 3,090,736 | 5/1963 | Bashaw et al. ............ 526/81 |
| 3,669,103 | 6/1972 | Harper et al. . |
| 3,670,731 | 6/1972 | Harmon . |
| 3,980,663 | 9/1976 | Gross . |
| 3,983,095 | 9/1976 | Bashaw et al. ............ 526/15 |
| 3,993,616 | 11/1976 | Gross . |
| 3,997,484 | 12/1976 | Weaver et al. . |
| 3,997,647 | 12/1976 | Lassen . |
| 4,043,952 | 8/1977 | Ganslaw et al. . |
| 4,090,013 | 5/1978 | Ganslaw et al. ............ 526/81 |
| 4,155,888 | 5/1979 | Mooth . |
| 4,172,066 | 10/1979 | Zweigle et al. ............ 604/368 |
| 4,192,727 | 3/1980 | Ward ............ 604/368 |
| 4,235,237 | 11/1980 | Mesek et al. ............ 604/368 |
| 4,295,987 | 10/1981 | Parks ............ 252/194 |

Primary Examiner—James C. Cannon
Attorney, Agent, or Firm—Paul A. Leipold; J. P. O'Shaughnessy

[57] ABSTRACT

The invention comprises of an anionic polyelectrolyte hydrogel reversibly cross-linked with a polyvalent metal cation having a valence of at least two. This hydrogel may be combined with a removal agent for imparting delayed swelling characteristics when contacted with a water-containing fluid. The delayed swelling allows the water-containing fluid to penetrate or permeate the system before swelling is initiated, thereby providing enhanced wetting prior to the onset of swelling and alleviating gel blockage.

19 Claims, 10 Drawing Figures

FIG. 1
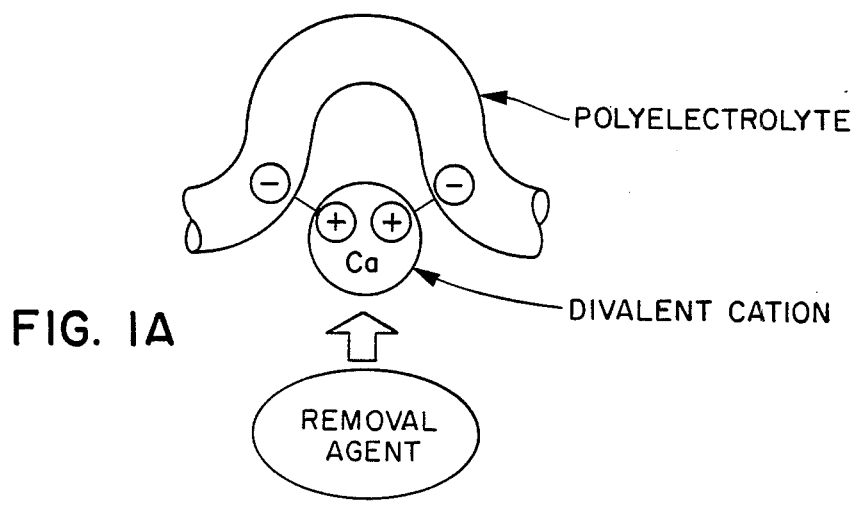
FIG. 1A
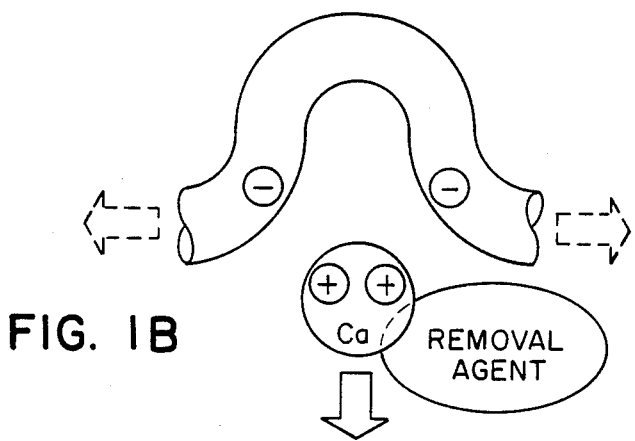
FIG. 1B
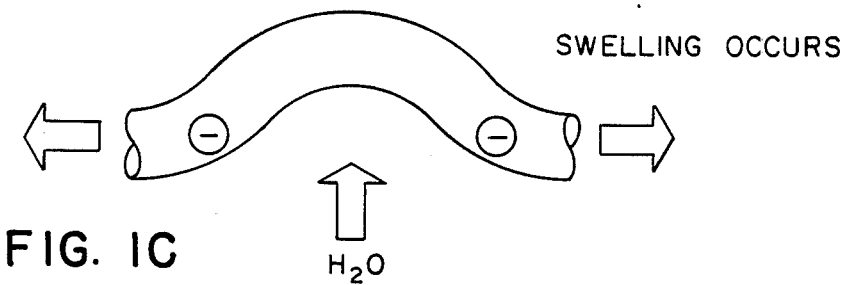
FIG. 1C

DELAYED-SWELLING ABSORBENT SYSTEMS

TECHNICAL FIELD

This invention relates to formation of water-swellable hydrogel absorbent systems and their use in articles such as absorbent pads, and other articles for absorption of aqueous solutions.

BACKGROUND ART

The past decade has seen the development of a class of absorbents having the ability to absorb many times their own weight in water or other aqueous solutions such as blood, urine and other body exudates.

These materials are commonly referred to as superabsorbents or hydrogels. They are generally prepared by polymerizing one or more monomers which when homopolymerized form a water-soluble polymer. To render them water-insoluble while maintaining their water-absorption characteristics, the polymers are typically cross-linked, either covalently or ionically, to introduce a limited water-insolubility while retaining susceptibility to swelling in water and water-containing fluids.

Typically superabsorbents are subject to the phenomenon known as "gel blocking". This term, as discussed in more detail below, refers to the restriction of further liquid-induced swelling of the remaining dry portion of the superabsorbent by that portion of the superabsorbent that is first contacted by the aqueous fluid. The portion first contacted by the aqueous fluid becomes swollen or gelled and restricts access of the fluid to the remaining dry portion of the superabsorbent. The result is that only a portion of the superabsorbent functions effectively as an absorbent with concomitant decreased efficiency and increased costs.

U.S. Pat. No. 4,043,952 teaches a method of improving the aqueous dispersability or wet-out of a water-absorbent composition based on an anionic polyelectrolyte polymer by surface treating the polyelectrolyte to ionically complex the exposed surface of the absorbent composition. In the words of U.S. Pat. No. 4,043,952, "The ionic complexing of the surface is believed to retard the formation of a surface gel which inhibits the passage of an aqueous fluid into the interior of the absorbent composition." This surface treatment of the anionic polyelectrolyte does not completely solve the gel-blocking problem where a body of the superabsorbent anionic polyelectrolyte is to be contacted with aqueous fluid and does not allow use of the entire water-absorptive properties of the gel.

U.S. Pat. No. 4,090,013 to Ganslaw et al. discloses a water-swellable, water-insoluble absorbent. It is an ionic complex of a water-soluble anionic polyelectrolyte and a polyvalent metal cation. The composition is characterized by an ability to uncomplex at elevated pH and then again complex at lower pH. The material acts as a gel maintaining its integrity at low pH as it swells with absorbed water. At higher pH, above about 8.5, the material becomes soluble. This feature is utilized as an aid in formation in materials, which may be extruded as a high pH liquid but which become a cross-linked material when the pH is lowered after extrusion.

There remains a need for a hydrogel material that is not subject to gel blocking. There further remains a need for a swellable hydrogel material that has a delayed-swelling action that permits permeation of the material by water. Further there remains a need for a low-cost formation method for formation of hydrogel materials.

DISCLOSURE OF THE INVENTION

It is an object of this invention to produce improved anionic polyelectrolyte hydrogel materials.

It is a further object of this invention to produce improved liquid absorbent pads.

It is a further object of this invention to produce an improved hydrogel with gel-blocking resistance.

These and other objects of the invention are generally accomplished by forming an anionic polyelectrolyte hydrogel reversibly cross-linked with a polyvalent metal cation having a valence of at least two. This hydrogel when subjected to the action of a water-soluble cation removing agent absorbs water in a delayed manner, thereby allowing water to pass through the reversibly cross-linked material, prior to removal of the cation by complexing with the removing agent and swelling of the gel.

The reversibly cross-linked hydrogel may be utilized in a variety of manners such as combined with fibrous materials and the water-soluble cation removing agent to form a pad. The pad when wet with an aqueous fluid will absorb water in a delayed manner as the removal agent removes the metal cation that is cross-linking the hydrogel and allows the hydrogel to swell after being substantially penetrated by the aqueous liquid.

In a preferred embodiment of the invention, the anionic polyelectrolyte is derived from starch as in U.S. Pat. No. 4,155,888 by reacting the starch, water, free-radical initiator and ethylenically unsaturated monomer. Then further treating the material with magnesium chloride to reversibly cross-link it with magnesium cations to the extent that the absorbent characteristics have been substantially reduced or eliminated. A preferred removal agent for the cross-linking cation is hexametaphosphate.

BRIEF DESCRIPTION OF THE DRAWINGS

FIGS. 1A, 1B, and 1C are illustrations of the cation removal process of the invention.

BEST MODE FOR CARRYING OUT THE INVENTION

Figure 2:
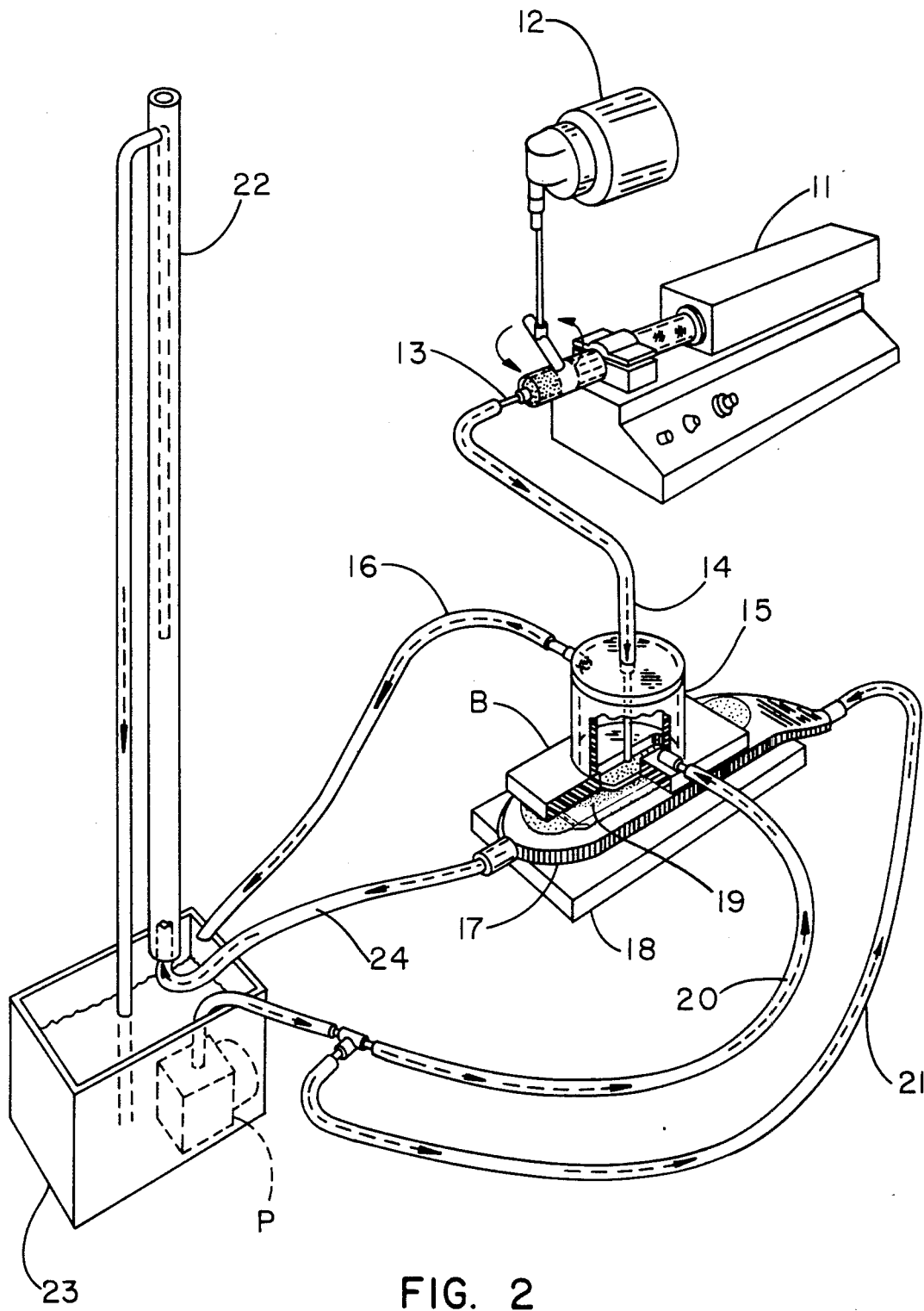
FIG. 2 is a prospective view of test apparatus in accordance with the tests of the examples.

The invention has numerous advantages over prior art systems. It allows the aqueous solution to be absorbed to penetrate the particles and/or layers of superabsorbent material prior to swelling and gel blocking taking place. Therefore, the materials of the invention have greater effective absorbent properties. The pads made by the invention are effective if used involving both high flow rates of aqueous solutions and in those instances where there is a slower rate of addition of aqueous fluids to the absorbent pad. Further, the reversibly ionically cross-linked hydrogel may be stored and shipped in a substantially nonabsorbent form, if the cation removal agent is not present with the hydrogel. This simplifies storage and handling of the material. Furthermore, production of this material is lower in cost as the high degree of cross-linking of the material allows it to absorb less water during formation and, therefore, less water removal is necessary during formation. These and other advantages of the invention directed to water-swellable absorbent hydrogels which have a time delay after exposure to an aqueous medium before substantial swelling is initiated will be apparent from the description below.

The absorbent systems of the invention comprise an anionic polyelectrolyte which is reversibly cross-linked with a polyvalent metal cation having a valence of at least two. The invention further includes the combination of the anionic polyelectrolyte which is reversibly cross-linked with a polyvalent metal cation having the valence of at least two and a source of a removal agent for the cross-linking cation. The function of the removal agent is to form a complex with the cross-linking agent, thereby removing it as a cross-linking material and substantially restoring the aqueous absorbing properties of the polyelectrolyte hydrogel.

The delayed swelling in the invention material occurs in the following manner: An aqueous fluid contacts the absorbent system. Since the anionic polyelectrolyte is cross-linked with the polyvalent metal cations, swelling is inhibited and the water-containing fluid is able to penetrate and permeate the absorbent. The aqueous fluid dissolves the water-soluble removal agent, following which the dissolved removal agent removes the polyvalent metal cations cross-linking the anionic polyelectrolyte, the uncross-linked anionic polyelectrolyte then may absorb the water-containing fluid and swell. That is, once polyvalent cations cross-linking the anionic polyelectrolyte are removed by the complexing agent, swelling of the anionic polyelectrolyte can proceed.

The term anionic polyelectrolyte hydrogel is conventionally defined and is used herein. An anionic polyelectrolyte hydrogel comprises a polymeric substance in which the monomeric units of its constituent macromolecules possess ionizable groups. These anionic groups include those such as carboxyls and sulfonates and the like.

The anionic polyelectrolytes useful in forming the absorbent of the invention include three classes: (1) water-soluble anionic polyelectrolytes. These are water-soluble hydrocolloid materials long known in the art, which increase in viscosity upon exposure to a fluid but which in the presence of an added fluid excess lose their power to retain the viscosities previously achieved; (2) water-swellable, water-insoluble covalently cross-linked anionic polyelectrolytes generally formed from one or more monomers, which as a homopolymer form a water-soluble polymer, which when covalently cross-linked has a limited water-insolubility. These anionic polyelectrolytes are generally characterized by the extent of cross-linking being such that the polymer network of the resulting hydrogel is not soluble in an aqueous media, yet remains flexible and swells as the aqueous media is absorbed within its structure (this type of anionic polyelectrolyte is described in U.S. Pat. Nos. 3,628,534; 3,669,103, and 3,670,731); and (3) water-swellable, water-insoluble ionic complexes of a water-soluble anionic polyelectrolyte and a polyvalent metal cation having a valence of at least three. The advantages of many of the ionic complex compositions over the covalently cross-linked compositions is that the ionic complex compositions are easy to shape and apply to substrates for particular applications since they may be uncomplexed at elevated pH and recomplexed at lower pH. All classes of the water-absorbent anionic polyelectrolyte hydrogels are suitable for the instant invention and may be utilized to provide a material that will alleviate the problem of gel blocking.

In the instant invention the anionic polyelectrolytes described above are further reversibly cross-linked with a polyvalent metal cation having a valence of at least two. The level of cross-linking is higher and more uniform than that conventionally used in superabsorbent anionic polyelectrolytes such as those disclosed in U.S. Pat. No. 4,043,952 and the cross-linking is reversible. Indeed, the level of reversible cross-linking is such that the swelling characteristics are substantially reduced or substantially eliminated, until the polyvalent metal cations cross-linking the anionic polyelectrolyte are removed. This level of cross-linking, as indicated above, is substantially greater than that normally contemplated by the superabsorbents discussed in the prior art.

The additional cross-linking referred to above may be accomplished in various way. Basically, however, the anionic polyelectrolytes are reversibly cross-linked by introducing a divalent or other multivalent cation into the anionic polyelectrolyte. This can be accomplished during the manufacture of the polyelectrolyte or by treating the preformed polyelectrolyte with an aqueous solution of the polyvalent metal cation.

The extent of increased cross-linking, and correspondingly the reduced degree of swelling, can be determined by a measurement of the anionic polyelectrolyte's salt retention value (SRV). The procedure for SRV determination is as follows: Approximately 0.12 grams of the anionic polyelectrolyte (calculated on oven-dry material) is placed in 30 milliliters of a 0.9 weight percent sodium chloride solutions and soaked for 10 minutes with gentle agitation. The resulting slurry comprised of the swollen polyelectrolytes (hydrogel) and excess water is then poured into a filtering centrifuge cup, which permits separation of external or excess water from the swollen hydrogel. Centrifugation is then carried out for 10 minutes under a force of 1,000 g's (where g is the unit of gravitational acceleration equal to the force exerted by gravity on a body at rest). After removal from the centrifuge, the water-swollen hydrogel remaining on the filter is weighed and then oven dried at 105 degrees C. following which it is weighed again. The weight of water absorbed, represented by the weight loss per gram of oven-dried material, is the SRV. Thus, the SRV represents the number of grams of water that are held by one gram of oven-dried superabsorbent by a force equal to or greater than the applied centrifugal force. By way of example, if 4.0 grams of the centrifuged material were dried at 105 degrees C. and then found on reweighing to weigh 0.12 grams, the weight of water absorbed represented by the weight loss in grams (4.0 grams−0.12 grams=3.88 grams) per gram of oven-dried material is the SRV. That is, on a per gram of oven-dried material, the SRV can be calculated from the following:

$$SRV = 3.88/0.12 = 32.3 \text{ gm/gm.}$$

Ionic cross-linking of the superabsorbent may be carried out during the sodium chloride soak by adding various concentrations of divalent or other polyvalent cations. The higher the concentration of the polyvalent ion, the greater degree of cross-linking. This phenomenon is demonstrated by the data set out in Table 1 below, obtained using the procedure described above with the sparingly cross-linked anionic polyelectrolyte (superabsorbent) Permasorb-10 available from National Starch and Chemical Corporation, cross-linked with calcium ions by addition of calcium chloride.

TABLE 1

Ca++ CROSS-LINKING OF PERMASORB-10

| Moles CA++/liter of 0.9 wt % NaCl | SRV |
| --- | --- |
| 0.005 | 25.49 |
| 0.006 | 18.06 |
| 0.011 | 12.21 |
| 0.027 | 2.63 |
| 0.045 | 1.50 |
| 0.063 | 1.27 |
| 0.090 | 1.23 |

As the level of calcium ions in the sodium chloride solution is increased, the level of cross-linking of the anionic polyelectrolyte superabsorbent is increased, resulting in a lower SRV. A lower SRV in turn indicates that there are fewer water molecules being held by the calcium ion cross-linked superabsorbent than the uncross-linked material, i,e., the absorbency of the material has been reduced.

The criteria for selecting the cross-linking metal ions are (1) that they have a charge opposite to the anionic polyelectrolyte's bound charges, i.e., that they be cations, (2) that they be polyvalent in nature, i.e., have a valence of at least two, and (3) that they are capable for reversibly cross-linking the anionic polyelectrolyte in such a manner that they are capable of being removed by a cation complexing agent, thereby returning the anionic polyelectrolyte to its absorbent form.

Any suitable polyvalent cation may be used in the process. Typical of suitable cations are magnesium and barium. A particularly preferred material is calcium as it is effective in cross-linking, safe, and readily combines with the complexing agents.

Various anionic polyelectrolytes, hydrogels or superabsorbents have different degrees of ionic swelling capability. A convenient method of evaluating SAMs for their relative degree of ionic swelling is to cross-link them with a polyvalent metal cation, such as calcium to a maximum extent, and compare the uncross-linked SRV with the cross-linked SRV. The comparison, expressed as a percentage:

$$(SRV_{cross-linked}/SRV_{uncross-linked} \times 100\%)$$

indicates the degree of swelling that may be controlled by ionic cross-linking. Table 2 lists some conventional anionic polyelectrolyte superabsorbents and their "degree of ionic swelling."

TABLE 2

DEGREE OF IONIC SWELLING

| Superabsorbent Source | SRV* Non-cross-linked** | SRV* Maximally Cross-linked | % Ionic Swelling |
| --- | --- | --- | --- |
| Aqualon C (Hercules Inc.) | 10.8 | 5.7 | 47 |
| Hoe S-2608 | 18.9 | 4.4 | 76 |
| GPC A100 (Grain Process.Corp.) | 16.5 | 3.1 | 81 |
| GPC A200 (Grain Process.Corp.) | 29.3 | 3.8 | 87 |
| XAP-147 (Henkel Corp.) | 21.9 | 2.3 | 90 |
| Stasorb-372 (A.E. Staley Mfg. Corp) | 39.5 | 2.5 | 94 |
| Permasorb-10 (Nat Starch & Chem Corp) | 25.4 | 1.3 | 95 |
| Sanwet IM-300 (SanyoChemCorp) | 39–54 | 1.5 | 96 |

*Units are gm-water/gm-superabsorbent
**Original Hydrogel

As noted above, once a sparingly cross-linked or uncross-linked anionic polyelectrolyte superabsorbent has been ionically cross-linked to the extent that the swelling characteristic has been substantially reduced, if not substantially eliminated, the cross-linked anionic polyelectrolyte may be returned to a state of high absorbency by removing the cross-linking cations. Removal of the cross-linking cations from their binding sites is accomplished by introducing a cation removing agent that forms a complex with the polyvalent metal cations which are cross-linking the anionic polyelectrolyte, thereby at least partially freeing the anionic sites and once again making the polyelectrolyte susceptible to swelling in the presence of a water-containing fluid. The cation removal agent should be sufficiently soluble in the water-containing fluid and form a complex with the polyvalent metal cations that is thermodynamically more stable than the complexes formed between the cations and the anionic polyelectrolyte.

Various types of material can function as the removal agent for the cross-linking cation. Generally, they are materials that complex with a polyvalent metal cation and neutralize its ionic charge, thereby effectively removing it from the environment of the anionic polyelectrolyte and neutralizing its interaction therewith. Such materials are referred to as ligands. A single ligand may be sufficient to form a charge neutralized complex with a cation or several ligands may be necessary. Further, several ligands may be connected together to form a chelate. A special group of ligands that charge neutralize, but form water-soluble compounds, are the sequestering agents. In some circumstances, sequestering agents are preferred since, because of their water solubility, they tend to carry the formed complex away from the anionic polyelectrolyte superabsorbent, thereby obviating the potential for a precipitated complex to block the structure and limit fluid permeation.

Compounds useful as the cation removing agent are potassium oxalate, sodium phosphate dibasic ($Na_2HPO_4$), i.e., the $HPO_4$ is the ligand, a chelate useful is the disodium salt of ethylenediamine-tetraacetic acid, and an inorganic sequestering agent useful in the subject invention is sodium hexametaphosphate (HMP). A number of other compositions may also be useful as the cation complexing agent in the subject invention.

Without being bound to any particular theory, the manner in which the absorbent systems of the subject invention function is believed more readily understood by consideration of the following.

The term "superabsorbent," as that term is used herein, refers generally to an anionic polyelectrolyte in which bound anionic groups within the polyelectrolyte provide the exceptional absorbency of these materials. Typically, the anionic bound groups are carboxyl functional groups acting as ionization centers. The mechanism of superabsorbency is believed to involve two physical phenomena: ionic solvation and electrostatic repulsion. Ionic solvation refers to the aqueous disassociation of the carboxyl group (or other anionic group) into a positively charged cation (M+) and a negatively charged functional group (e.g., —COO−). Both types of disassociated ions are hydrated or surrounded by clusters of water molecules. Solvated cations are highly mobile in the water-containing fluid and rapidly become distributed throughout the entire solution. The carboxyl groups (or other anionic groups) are attached to the polymer backbound and are not mobile. Being of similar charge, however, they repel each other and force the polymer to expand. As polymer expansion proceeds, more carboxyl groups become available for solvation and larger clusters of water molecules can surround each solvated group.

This polymeric expansion is referred to as swelling. There is a very noticeable increase in volume of the material. As it absorbs more water, the anionic polyelectrolyte superabsorbent becomes less solid and more gel-like. The anionic polyelectrolyte is effectively dissolving into the water, leaving the solid phase and entering the liquid phase. It would completely enter the liquid phase if it were not for covalent bonding or, if present, polyvalent cationic cross-links between the polymer chains. The degree of covalent cross-linking can be synthetically controlled to produce materials that gel to any desirable consistency, from relatively solid to virtually liquid. Indeed, as indicated above, the anionic polyelectrolytes useful in the subject invention include water-soluble anionic polyelectrolytes where substantially no cross-linking or covalent bonding from one polymer chain to another is present. However, the latter's use is preferably limited to the situation where only limited amounts of water are introduced into the composition of matter, i.e., less than that required to dissolve them.

The anionic polyelectrolytes useful in the subject invention are reversibly cross-linked with polyvalent metal cations having a valence of at least two. The anionic polyelectrolytes generally have covalent or ionic bonds present prior to farther cross-linking with metal cations in accordance with the invention. The resulting compositions have substantially reduced absorption capabilities resulting from this cross-linking. The result is that aqueous fluids are able to penetrate or permeate the cross-linked anionic polyelectroltye since the swelling and concomitant gel blocking are substantially reduced or even eliminated by virtue of the reduced absorption characteristics of the polyelectrolyte. However, when the absorbent systems of the subject invention comprise a second component, i.e., the cation removal agent, (1) which is soluble in the water-containing fluid, and (2) in the presence of a water-containing fluid is capable of reacting with the polyvalent metal cations cross-linking the anionic polyelectrolyte, the cation removal agent is dissolved by the water-containing fluid and then, in turn, removes the polyvalent metal cations from the cross-linked anionic polyelectrolyte, complexes them, thereby neutralizing their charge, and effectively removing them as a cross-linking factor in the hydrogel of the subject invention. The swelling of the anionic polyelectrolyte then proceeds in conventional manner, i.e., the no longer bound anionic charges of the anionic polyelectrolyte repulse each other, extend to the extent permitted by the initial sparsely distributed cross-links that have not been removed, thereby allowing the polyelectrolyte to absorb water molecules until an expanded gel is obtained. However, because of the time delay in initiation of the swelling of the anionic polyelectrolyte, the water-containing fluid has been able to penetrate and permeate throughout the mass of the anionic polyelectrolyte.

The operation of the invention is illustrated by the FIG. 1 drawings. As represented in FIG. 1A, the polyelectrolyte hydrogel material is cross-linked by a calcium divalent cation. The removal agent is brought into contact with the calcium cross-linked hydrogel and forms a complex with the calcium, removing it from the hydrogel polymer, as illustrated in 1B. In the IC figure, the polymer is free to expand and absorb water, as the cross-linking restriction is no longer applied as the polyvalent cation has been removed.

The following examples which are provided by way of illustration will serve to further explain the nature of the invention. The cation removal agent is generally referred to in the examples as the cation complexing agent (CCA).

EXAMPLES 1–6

In Examples 1–6 the ability of a cation complexing agent to restore the swelling characteristics of a cross-linked anionic polyelectrolyte (superabsorbent), Stasorb-372, is demonstrated. Some difficulty is encountered in showing the extent of the restoration, however, since the weight of a precipitated metal cation complex formed by the reaction of the cation complexing agent with the cross-linking cation of the polyelectrolyte is retained and increases the apparent dry weight of the superabsorbent. The result is an apparent SRV that is too low because the ratio of absorbed water to dry polymer (superabsorbent) mass has been reduced by the inclusion of the mass of the cation complexing agent.

One solution to this problem is to use a sequestering agent that does not form a precipitate. However, even in this situation, the apparent extra weight of the absorbed water must be corrected to yield the proper ratio of water to dry polymer (superabsorbent) mass.

In Table 3 below, sodium hexametaphosphate (HMP) was used to reswell Stasorb-372 cross-linked with either $Ca^{++}$ or $Mg^{++}$ as indicated. As will be evident from Table 3, the measured SRV of the superabsorbent material (SAM) is approximately one-third the value of the uncross-linked SAM even though by visual inspection all SAMs had obviously been reswollen. By accounting for the mass of HMP in solution by the method set out below, corrected SRVs can be obtained that are commensurate with the visual observations.

TABLE 3

| RESWOLLEN SALT RETENTION VALUES | | | | |
|---|---|---|---|---|
| Example | Cation | Moles/Liter | $(SRV)_m$ | $(SRV)_c$ |
| 1 | $Ca^{++}$ | 0.050 | 9.77 | 28.02 |
| 2 | $Ca^{++}$ | 0.025 | 10.39 | 33.81 |
| 3 | $Ca^{++}$ | 0.012 | 10.71 | 37.57 |
| 4 | $Mg^{++}$ | 0.050 | 9.87 | 28.86 |
| 5 | $Mg^{++}$ | 0.025 | 10.03 | 30.27 |
| 6 | $Mg^{++}$ | 0.014 | 10.32 | 33.08 |

Reswelling agent used: Sodium hexametaphosphate (HMP)
Superabsorbent material (SAM) used: Stasorb-372
Original precross-linked SRV for Stasorb-372 = 39.5 gm-water/gm-SAM TABLE 3-continued

| RESWOLLEN SALT RETENTION VALUES | | | | |
|---|---|---|---|---|
| Example | Cation | Moles/Liter | $(SRV)_m$ | $(SRV)_c$ |

$SRV_m$ refers to the measured SRV
$SRV_c$ refers to the corrected SRV
Derivation of SRV correction:
$(SRV)_m =$ SRV as measured after swelling
$(SRV)_c =$ Corrected SRV
$X =$ Weight of water in SAM
$P =$ Weight of SAM (Stasorb-372)
$A =$ Weight fraction of HMP in solution (A = 0.067)
$(SRV)_m = X/(P + AX)$
$1/(SRV)_m = (P/X) + A$
$(SRV)_c = X/P$
$1/(SRV)_c = 1/(SRV)r - A$

EXAMPLES 7-36

Sanitary products for human use are typically comprised of garment-like appliances whose function is to collect and retain body fluids, chiefly urine and menstrual fluids. The major absorption element in these products is generally a fibrous material, usually cellulose, having a network of fluid-retaining capillaries. The inclusion of a superabsorbent in these products increases the amount of fluid that can be retained before the total saturation point is reached. The following examples demonstrate the use of the compositions of matter of the subject invention in such sanitary products.

In the following examples, heparinized bovine blood was used instead of saline solution. Bovine blood is used as a mimic for human menstrual fluid. The bovine blood was applied into the fiber network from a syringe pump at a flow rate of 3 gm/hr using the apparatus shown in FIG. 2 and the procedure described below.

Absorbency in a fibrous network is measured with the same physical units as the SRV, as described above, that is, the weight of fluid retained per dry weight of absorbent. There are, however, geometric constraints in a fiber network that make interpretation of these parameters more subtle. In SRV determinations, an excess of fluid is present in relation to absorbent; in fibrous-network determinations, an excess of absorbent is present in relation to fluid. An excess of fluid is easily removed but it is not possible to cleanly remove an excess of absorbent. The excess absorbent is effectively removed, however, by considering only that material that is stained by the fluid. In order to do this, the dry bases weight of the absorbent in a product must be known.

As an experimental standard, the basis weight of the cellulose fiber network (a two-inch square of material) was held constant at 30 gm/ft² in all the following experiments. The amount of both the cross-linked superabsorbent material (SAM) and the cation complexing agent (CCA) incorporated into the fiber network was varied. The absorbency parameter is then $C_f$ (gm-blood/gm-fiber) which is equivalent to the amount of blood per unit area of fiber network.

The testing apparatus used (FIG. 2) consists of a variable rate syringe pump and means for maintaining constant temperature and pressure on the sample. The fluid utilized for testing is heparinized bovine blood which has its hematocrit, i.e., red blood cell level, adjusted to a level of twenty volume percent of the solution. The blood is fed by the pump 11 past a magnetic stirrer 12 through a syringe ejector 13 and into intake tube 14. Intake tube 14 leads into a hollow-walled heat exchanger 15 which, as shown in partial cross section, rests upon a supporting block B which in turn rests upon the two-inch square sample 19 being treated. A colostomy bag 17 is located beneath the sample and sits upon a support 18. The colostomy bag is fluidly connected with the constant temperature bath 23 through colostomy intake tube 21 via pump P. As shown in the drawings, pump P also provides the heat exchanger 15 with a temperature controlled water flow through water intake tube 20. Stand pipe 22 is also connected to the colostomy bag by pressure tube 24. The stand pipe, in conjunction with the constant temperature bath 23, controls both temperature and pressure. The sample is maintained at a constant temperature of 37 degrees C., which is body temperature, by means of the constant temperature bath-generated fluid flow into the heat exchanger 15 through line tube 20 (with the fluid exiting from the heat exchanger jacket through exit conduit 16) and also through the flow through tube 21 into the colostomy bag 17. The pressure is maintained at seventy-five centimeters of water and the flow of the modified bovine blood is maintained for one hundred twenty minutes at a flow rate of three milliliters per hour. The absorbency parameter $G_f$ was calculated after the test was completed.

Table 4 summarizes the data collected in this series of experiments. The data was statistically analyzed through linear regression as a two-factor design with interactions. The result was a predictive equation whose coefficients assess the magnitude of the effect for each factor or interaction. The equation determined was:

$$G_f = 3.8 + 0.4(CCA) + 2.0(SAM) + 19.1(CCA)(SAM) \quad (1)$$

Table 5 presents the regression summary for the data from Table 4. From Table 5 it is evident that the interaction coefficient is the most important, having the largest value (19.1). This indicates that the system is functioning as a two-component system. It also demonstrates that a cross-linked SAM does reswell from the action of the cation complexing agent dissolved in a blood-like fluid as it flows through a fibrous network. Another way of demonstrating reswelling is to take the derivative of Equation (1) with respect to the concentration of SAM. Thus:

$$dG_f/dSAM = 2.0 + 19.1(CCA) \quad (2)$$

Equation (2) demonstrates that the presence of the cation complexing agent increases the absorption of a fibrous-network/cross-linked-SAM composite in direct proportion to the concentration of the cation complexing agent at all SAM concentrations.

TABLE 4

| FIBROUS NETWORK ABSORPTION | | | | | | | |
|---|---|---|---|---|---|---|---|
| | | | $G_f$ | | | | |
| Example | CCA | SAM | 1 | 2 | 3 | 4 | Average |
| 7 | .120 | .606 | 6.03 | 6.50 | 6.53 | 6.25 | 6.33 |
| 8 | .120 | .303 | 5.17 | 5.52 | 5.48 | 5.42 | 5.40 |
| 9 | .120 | .202 | 5.19 | 5.00 | 5.20 | 5.73 | 5.28 |
| 10 | .461 | .187 | 6.73 | 5.64 | 5.69 | 6.08 | 6.04 |
| 11 | .311 | .187 | 5.72 | 5.58 | 5.91 | 6.04 | 5.81 |
| 12 | .154 | .187 | 5.43 | 5.25 | 5.37 | 5.56 | 5.40 |
| 13 | 0.0 | .606 | 5.10 | 4.90 | 4.71 | 5.09 | 4.95 |
| 14 | 0.0 | .303 | 4.05 | 4.12 | 4.35 | 4.34 | 4.22 |
| 15 | 0.0 | .202 | 4.55 | 4.51 | 4.33 | 4.65 | 4.51 |
| 16 | .150 | .303 | 5.68 | 5.56 | 5.81 | 5.09 | 5.54 |
| 17 | .075 | .303 | 4.31 | 4.66 | 5.04 | 4.55 | 4.63 |
| 18 | .060 | .303 | 4.62 | 4.06 | 4.23 | 4.25 | 4.29 |

TABLE 4-continued

FIBROUS NETWORK ABSORPTION

| | | | $G_f$ | | | | |
|---|---|---|---|---|---|---|---|
| Example | CCA | SAM | 1 | 2 | 3 | 4 | Average |
| 19 | .120 | .303 | 5.31 | 5.20 | 4.9$ | 4.61 | 5.01 |
| 20 | 0.0 | .303 | 4.51 | 4.10 | 4.61 | 4.27 | 4.37 |
| 21 | 0.0 | .187 | 4.27 | 4.40 | 4.49 | 4.81 | 4.4$ |
| 22 | 0.0 | 0.0 | 4.17 | 3.56 | 3.91 | 3.84 | 3.73 |
| 23 | 0.0 | .186 | 4.32 | 4.58 | 4.56 | 4.49 | 4.49 |
| 24 | .071 | .186 | 4.95 | 4.83 | 5.09 | 5.33 | 5.05 |
| 25 | .155 | .186 | 5.04 | 4.96 | 5.32 | 5.17 | 5.12 |
| 26 | .221 | .186 | 5.14 | 5.08 | 6.12 | 5.13 | 5.37 |
| 27 | .290 | .186 | 5.85 | 5.60 | 5.55 | 5.28 | 5.57 |
| 28 | .376 | .186 | 5.51 | 5.27 | 5.02 | 5.41 | 5.30 |
| 29 | .442 | .186 | 5.40 | 5.43 | 5.83 | 5.76 | 5.61 |
| 30 | 0.0 | 0.0 | 3.50 | 4.10 | 3.76 | 3.28 | 3.66 |
| 31 | .071 | 0.0 | 3.40 | 3.37 | 3.47 | 3.41 | 3.41 |
| 32 | .155 | 0.0 | 3.51 | 3.71 | 3.84 | 3.57 | 3.66 |
| 33 | .221 | 0.0 | 3.84 | 4.67 | 3.57 | 3.67 | 3.94 |
| 34 | .290 | 0.0 | 3.89 | 4.63 | 3.54 | 3.64 | 3.93 |
| 35 | .376 | 0.0 | 4.12 | 4.07 | 3.74 | 4.12 | 4.01 |
| 36 | .442 | 0. | | | | | |
| 0 | 4.32 | 4.08 | 3.82 | 4.04 | 4.07 | | |

Units: Gf = gm-blood/gm-fiber
CCA = gm-CCA/gm-fiber
SAM = gm-SAM/gm-fiber
Basis weight of fibrous network: 30 gm/ft$^2$
Superabsorbent used: Permasorb-10
Cross-linking agent: Calcium cations
Fluid: Bovine blood infused at a rate of 3 gm/hr
Cationic complexing agent: Hexametaphosphate (HMP)
Infusion time: 2 hr, 1 hr equilibration

TABLE 5

REGRESSION SUMMARY FOR EQUATION (1)

| Variable | Estimate | SE | t-value |
|---|---|---|---|
| Intercept | 3.8454 | 0.0724 | 53.11 |
| CCA | 0.4180 | 0.3487 | 1.20 |
| SAM | 2.0232 | 0.2854 | 7.09 |
| CCA × SAM | 19.1213 | 1.9901 | 9.61 |

$a^2 = 0.1466$; df = 127; $R^2 = 0.792$

OVERALL ANALYSIS OF VARIANCE

| Source | df | SS | MS | F |
|---|---|---|---|---|
| Regression | 3 | 69.340 | 23.11 | 157.6 |
| Residual | 124 | 18.180 | 0.1466 | |
| Total | 127 | 87.520 | | |
| Residual: fit | 23 | 10.126 | 0.440 | 5.518 |
| Error | 101 | 8.054 | 0.080 | |
| Total | 124 | 18.180 | | |

From the data presented above, it has been shown that superabsorbents can be cross-linked by the incorporation of a polyvalent metal cation and then aqueous absorbing properties increased by a cation removal agent. Intuitively, it is obvious that the action of dissolving by the reswelling agent will involve a delay in the swelling response time of the cross-linked superabsorbent. However, it is the purpose of the following examples 37-68 to demonstrate the reality of this time delay, as well as its benefit.

The following experiments were designed to demonstrate delayed reswelling in a cellulose fiber/cross-linked superabsorbent composite structure by showing a response to fluid flow rate with and without the presence of a cation complexing agent. The experiments were given a two factor design: two levels of cation complexing agent and two fluid flow rates. In these experiments HMP was used as the cation complexing agent. A control, noncross-linked superabsorbent, was utilized under identical conditions for comparison. Table 6 presents the data for this set of experiments.

An analysis of the data for the noncross-linked superabsorbent demonstrated that there was no statistical change in the value of $G_f$ when either flow rate or cation complexing agent was varied. The statistical analysis is given in Table 7.

For the cross-linked SAM, quite different results were obtained. Here there is a definite relationship between $G_f$ and the two experimental factors of rate (FR) and cation complexing agent (CCA). The relationship found was:

$$G_f = 3.7 + 9.5(CCA) + 0.2(FR) - 1.4(CCA)(FR) \quad (3)$$

The statistical analysis is presented in Table 8. Equation (3) is virtually identical to Equation (1) at identical conditions (FR=3 gm/hr; SAM=0.186 gm/gm-fiber). They both predict a linear increase in $G_f$ with reswelling agent ($G_f \approx 4.3 + 4.5(CCA)$). With regard to flow rate, Equation (3) predicts that flow rate alone has no significant effect; however, a strong interaction between flow rate (FR) and the level of cation complexing agent (CCA) is found.

Figure 3:
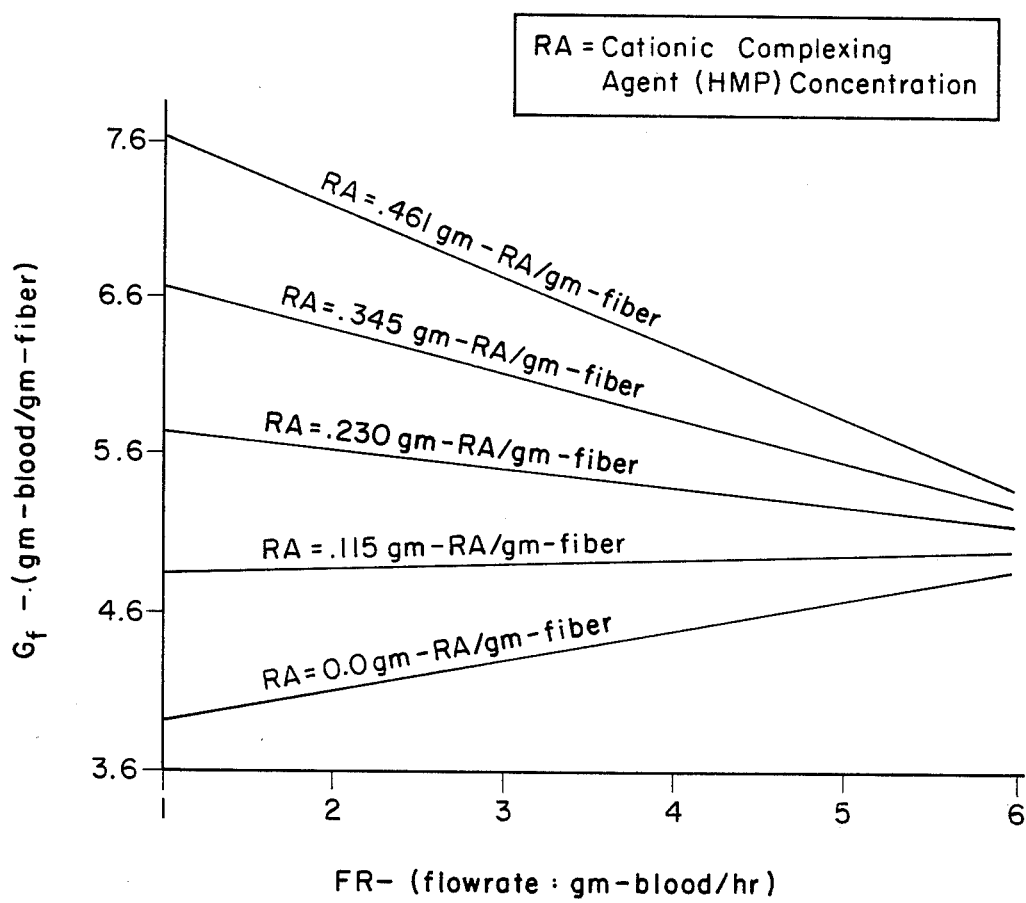
FIG. 3 is a graph illustrating the increased absorption of the invention material.

FIG. 3 is a graphical depiction of Equation (3) where $G_f$ is plotted against flow rate (FR) for various cation complexing agent concentrations. The fact that the values of $G_f$ drop at higher flow rates indicates that delayed reswelling does occur. The explanation for this conclusion is that the rate of absorption of the cross-linked SAM is initially very slow. The fluid in the fiber network is dispersed primarily by the fibers alone. The values for $G_f$ thus tend to approach the low values that are obtained for fiber networks without SAMs ($G_f = 3.7$). As the cross-linked SAMs reswell from the action of the dissolved cation complexing agent, the SAM absorbency rate increases causing the value of $G_f$ to also increase as more fluid flows into the fiber/SAM composite. The value of $G_f$ finally obtained is intermediate between the low value for fibers alone and the high value for uncross-linked SAM ($G_f$ for Permasorb-10=6.2). But, because the reswelling of the cross-linked SAM is dependent on the dissolution of the cation complexing agent, the greater the fluid flow rate, the greater the volume of fluid that is dispersed by fiber mechanisms alone before reswelling. Therefore, a reduction in the value of $G_f$ as fluid flow rate increases is an indication of a delayed SAM swelling.

A material that responds in this fashion is useful in coping with stressful (high flow rate) situations. The phenomenon of gel blocking is reduced, a valuable attribute of compositions and articles of this invention since a product that has gel blocked is of limited value to its user because the entire product absorbs at the very slow rate of the SAM alone. A product containing the composition of the subject invention avoids gel blocking.

TABLE 6

FLOWRATE RESPONSE EXPERIMENTS

| Example | SAM Type | CCA | FR | $G_f$ |
|---|---|---|---|---|
| 37 | Cross-linked | 0 | 3 | 3.95 |
| 38 | Cross-linked | 0 | 3 | 4.38 |
| 39 | Cross-linked | 0 | 3 | 4.43 |
| 40 | Cross-linked | 0 | 3 | 4.33 |
| 41 | Uncross-linked | 0 | 3 | 7.41 |
| 42 | Uncross-linked | 0 | 3 | 5.67 |
| 43 | Uncross-linked | 0 | 3 | 7.05 |
| 44 | Uncross-linked | 0 | 3 | 6.42 |
| 45 | Cross-linked | 0.461 | 3 | 6.83 |
| 46 | Cross-linked | 0.461 | 3 | 6.56 |
| 47 | Cross-linked | 0.461 | 3 | 6.13 |
| 48 | Cross-linked | 0.461 | 3 | 7.32 |
| 49 | Uncross-linked | 0.461 | 3 | 5.55 |

TABLE 6-continued

FLOWRATE RESPONSE EXPERIMENTS

| Example | SAM Type | CCA | FR | $G_f$ |
|---|---|---|---|---|
| 50 | Uncross-linked | 0.461 | 3 | 5.41 |
| 51 | Uncross-linked | 0.461 | 3 | 5.55 |
| 52 | Uncross-linked | 0.461 | 3 | 6.30 |
| 53 | Cross-linked | 0 | 6 | 4.62 |
| 54 | Cross-linked | 0 | 6 | 4.97 |
| 55 | Cross-linked | 0 | 6 | 5.64 |
| 56 | Cross-linked | 0 | 6 | 4.28 |
| 57 | Uncross-linked | 0 | 6 | 6.29 |
| 58 | Uncross-linked | 0 | 6 | 6.12 |
| 59 | Uncross-linked | 0 | 6 | 6.15 |
| 60 | Uncross-linked | 0 | 6 | 6.17 |
| 61 | Cross-linked | 0.461 | 6 | 5.62 |
| 62 | Cross-linked | 0.461 | 6 | 5.58 |
| 63 | Cross-linked | 0.461 | 6 | 5.29 |
| 64 | Cross-linked | 0.461 | 6 | 5.07 |
| 65 | Uncross-linked | 0.461 | 6 | 5.62 |
| 66 | Uncross-linked | 0.461 | 6 | 5.84 |
| 67 | Uncross-linked | 0.461 | 6 | 5.45 |
| 68 | Uncross-linked | 0.461 | 6 | 5.69 |

Units: CCA = gm-CCA/gm-fiber
*SAM AS IS
FR = gm-blood/hr
$G_f$ = gm-blood/gm-fiber
Basis weight of fibrous network: 30 gm/ft$^2$
Superabsorbent used: Permasorb-10
Cross-linking agent: Calcium cations
Fluids Bovine blood

TABLE 7

REGRESSION SUMMARY FOR UNCROSS-LINKED PERMASORB-10

| Variable | Estimate | SE | t-value |
|---|---|---|---|
| Intercept | 7.092 | 0.493 | 14.485 |
| CCA | −2.901 | 1.513 | −1.917 |
| FR | −0.152 | 0.104 | −1.462 |
| CCA × FR | 0.291 | 0.319 | 0.912 |

$\sigma^2 = 0.194$; df − 15; $R^2 = 0.524$

OVERALL ANALYSIS OF VARIANCE

| Source | df | SS | MS | F |
|---|---|---|---|---|
| Regression | 3 | 2.573 | 0.858 | 4.409 |
| Residual | 12 | 2.335 | 0.195 | |
| Total | 15 | 4.908 | | |

TABLE 8

REGRESSION SUMMARY FOR EQUATION (3)

| Variable | Estimate | SE | t-value |
|---|---|---|---|
| Intercept | 3.668 | 0.468 | 7.838 |
| CCA | 9.468 | 1.435 | 6.594 |
| FR | 0.202 | 0.099 | 2.040 |
| CCA × FR | −1.392 | 0.302 | −4.609 |

$\sigma^2 = 0.175$; df = 15; $R^2 = 0.860$

OVERALL ANALYSIS OF VARIANCE

| Source | df | SS | MS | F |
|---|---|---|---|---|
| Regression | 3 | 12.924 | 4.308 | 24.617 |
| Residual | 12 | 2.100 | 0.175 | |
| Total | 15 | 15.024 | | |

The examples set out above establish that time delayed swelling characteristics can be imparted to an anionic polyelectrolyte (superabsorbent) by reversibly cross-linking. The resulting compositions of matter have the desirable property of conventional superabsorbents, i.e., the ability to absorb many times their own weight in water or water-containing fluids coupled with a time delay before absorption (swelling) is initiated, the latter permitting permeation of the system with the fluid and thereby alleviating gel blockage.

INDUSTRIAL APPLICABILITY

The composition of the subject invention find use in a variety of products where the ability to absorb a large quantity of water or water-containing fluid is desirable. Examples include disposable diapers, surgical pads and sheets, paper towels, sanitary products, such as sanitary napkins, hospital bed pads, absorbent dressings and the like. Typical liquids which are effectively absorbed by the compositions of the subject invention include water and water-containing fluids such as urine, blood and other water-containing fluid body exudates.

Figure 4:
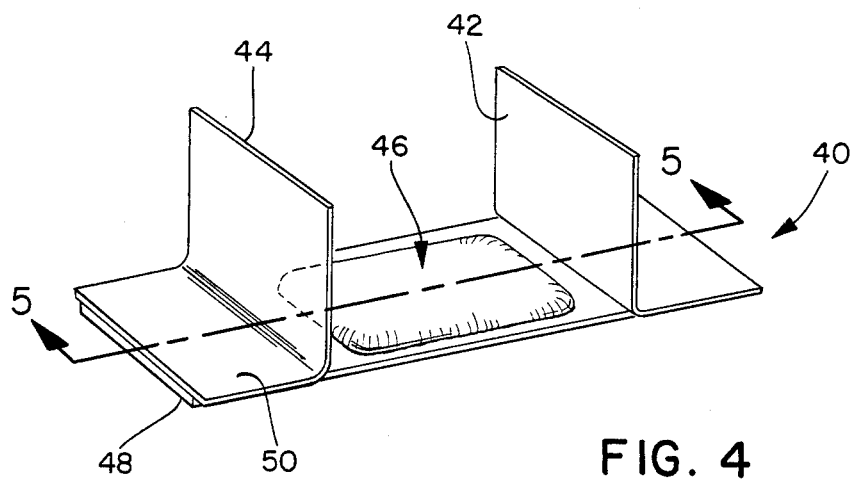
FIG. 4 is a prospective view of a dressing utilizing the invention.
Figure 5:
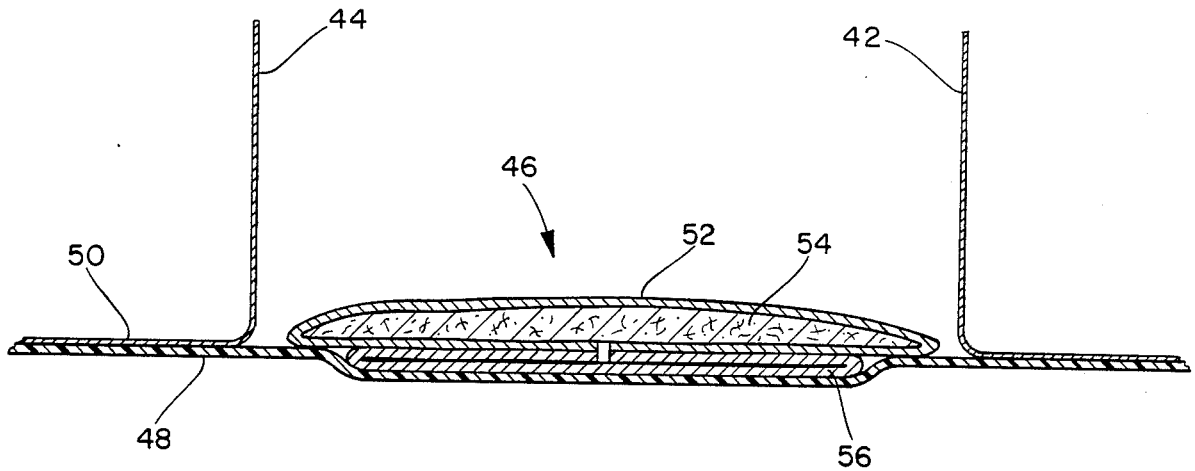
FIG. 5 is a cross-section of the dressing of FIG. 4 taken on line 5—5.

The compositions of the invention may be utilized in a wound dressing such as illustrated in FIGS. 4 and 5. FIG. 4 illustrates a wound dressing generally identified as 40. The wound dressing has protective flaps 42 and 44 to preserve the sterile characteristics of the pad 46. As illustrated in FIG. 5, the pad 46 rests on substrate 48 that has an adhesive layer on its surface 50. The pad 46 is comprised of a porous surface layer 52, on absorbent nonwoven material 54 immediately below porous layer 52 and a second layer of porous material 56 underlying porous layer 54. The hydrogel of the invention would be usually incorporated into layer 56, although in view of the penetrating properties of the instant invention, the gel-forming material could be incorporated into both layers 54 and 56, or only one absorbent layer utilized.

Figure 6:
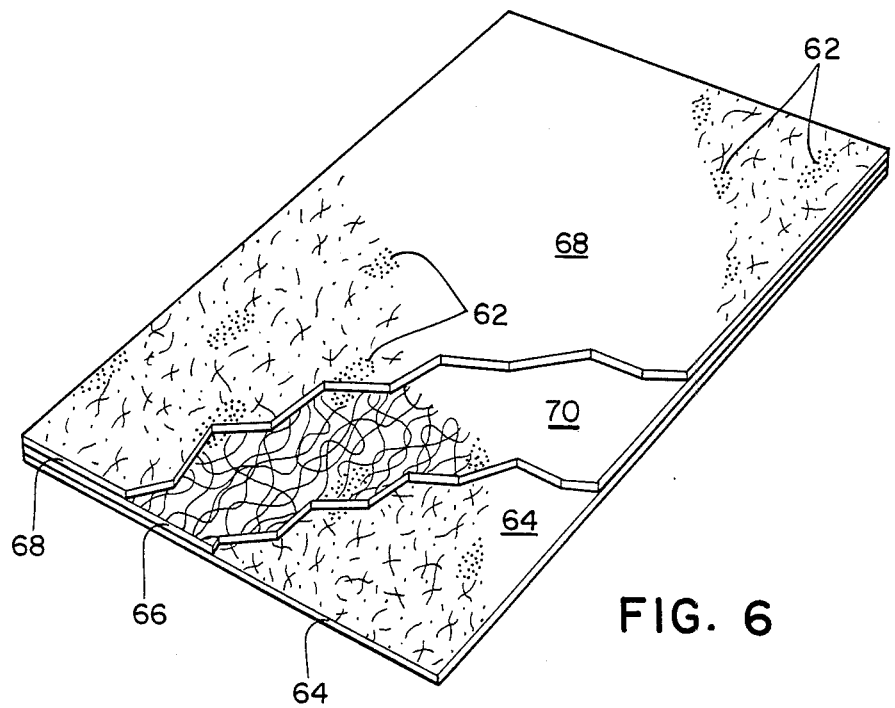
FIG. 6 is a pad having areas of the invention absorbent located therein.

In FIG. 6 absorbent pad 60 is formed of several layers—64, 66, and 68. These layers each have discrete areas 62 of the superabsorbent material of the invention placed on to the sheet prior to formation of the composite pad.

Figure 7:
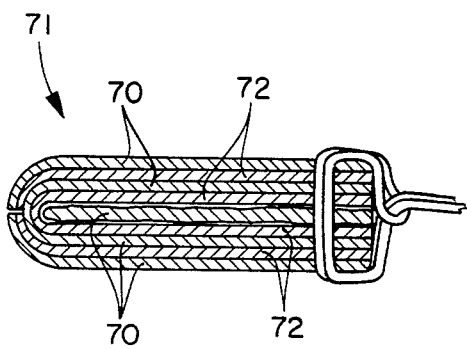
FIG. 7 is a tampon utilizing material of the invention.

In FIG. 7 is illustrated a tampon 71 in which porous layers 70 allow menstrual fluids to flow into the tampon where the absorbent layers 72 containing the material of the invention absorb the fluids.

Figure 8:
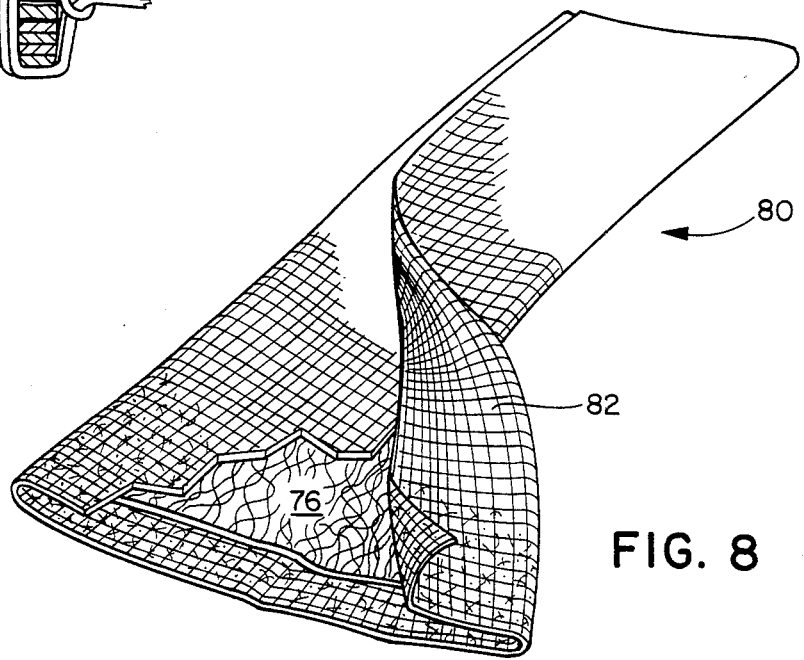
FIG. 8 is a pad in which an inner fibrous layer contains absorbent of the invention.

In FIG. 8 is illustrated a pad 80, having a surface wrapped in a fabric 82, having large openings. The inner nonwoven material 76 has the superabsorbent of the invention incorporated therein.

These are representative of articles formed in accordance with the invention; however, it will be clear to those skilled in the art that the superabsorbence of the invention may be incorporated in other devices for absorption of aqueous materials, including diapers and menstrual pads.

We claim:

1. An article of manufacture comprising an open support structure containing a water-swellable, water-absorbent system comprising an anionic polyelectrolyte reversibly cross-linked with polyvalent metal cations having a valence of at least two and a cation removal agent which upon contact with water-containing fluid is soluble therein and capable of reacting or complexing with the polyvalent metal cations cross-linking the anionic polyelectrolyte to thereby provide said system with delayed swelling characteristics when contacted with water-containing fluid, said system having delayed swelling characteristics when contacted with a water-containing fluid.

2. The article of claim 1 wherein said cation removal agent comprises a ligand.

3. The article of claim 1 wherein said cation removal agent is selected from the group consisting essentially of sodium phosphate dibasic, the disodium salt of ethylenediamine-tetraacetic acid, sodium hexametophosphate and mixtures thereof.

4. The article of claim 1 wherein said anionic polyelectrolyte is partially cross-linked by another means in addition to said metal cation.

5. The article of claim 1 wherein said open support structure is a fibrous mat.

6. A water-swellable, water-absorbent system comprising an anionic polyelectrolyte reversibly cross-linked with polyvalent metal cations having a valence of at least two and a cation removal agent which upon contact with water-containing fluid is soluble therein and capable of reacting or complexing with the polyvalent metal cations cross-linking the anionic polyelectrolyte to thereby provide said system with delayed swelling characteristics when contacted with water-containing fluid, said system having delayed swelling characteristics when contacted with a water-containing fluid.

7. The system of claim 6 wherein said cation removal agent comprises a ligand.

8. The system of claim 6 wherein said cation removal agent is selected from the group consisting essentially of sodium phosphate dibasic, the disodium salt of ethylenediaminetetraacetic acid, sodium hexametophosphate and mixtures thereof.

9. The system of claim 6 wherein said anionic polyelectrolyte is partially cross-linked by another means in addition of said metal cation.

10. A method for the absorption of a water-containing fluid comprising contacting said fluid with the system of claim 1.

11. A water-absorbing system comprising substantially nonabsorbent anionic polyelectrolyte reversibly cross-linked with polyvalent metal cations having a valence of at least two (2) and a cation removal agent which upon contact with water-containing fluid is soluble therein and capable of reacting or complexing with the polyvalent metal cations cross-linking the anionic polyelectrolyte to thereby provide said system with delayed swelling characteristics when contacted with water-containing fluid.

12. The system of claim 11 wherein said anionic polyelectrolyte is partially cross-linked by another means in addition to the cross-linking of said metal cation.

13. The system claim 11 wherein said cation comprises magnesium, barium, or combinations thereof.

14. The system of claim 11 wherein said cation comprises calcium.

15. The combination of claim 11 wherein said cation removal agent is selected from the group consisting essentially of sodium phosphate dibasic, the disodium salt of ethylenediamine-tetraacetic acid, sodium hexametophosphate and mixtures thereof.

16. A method for preparing an anionic polyelectrolyte reversibly cross-linked with a polyvalent metal cation to an extent that the superabsorbency characteristics of said polyelectrolyte have been substantially reduced comprising providing an imcompletely cross-linked anionic polyelectrolyte, contacting said polyelectrolyte with an aqueous solution of a salt of a polyvalent metal cation to complete cross-linking and form substantially nonabsorbent material, removing water to recover cross-linked polyelectrolyte and combining said cross-linked recovered polyelectrolyte with a cation removal agent under conditions such that said removal agent does not react or complex with the polyvalent metal cations cross-linking said polyelectrolyte.

17. The method of claim 16 wherein said anionic polyelectrolyte is partially cross-linked by another means prior to reversible cross-linking with said metal cation.

18. The method of claim 16 wherein said cation comprises magnesium, barium, or combinations thereof.

19. The method of claim 16 wherein said cation comprises calcium.

* * * * *